United States Patent [19]

Frank et al.

[11] Patent Number: 4,606,940

[45] Date of Patent: Aug. 19, 1986

[54] SMALL PARTICLE FORMATION AND ENCAPSULATION

[75] Inventors: Sylvan G. Frank, Columbus, Ohio; Arne F. Brodin, Sodertalje, Sweden; Shulin Ding, Columbus, Ohio

[73] Assignee: The Ohio State University Research Foundation, Columbus, Ohio

[21] Appl. No.: 684,457

[22] Filed: Dec. 21, 1984

[51] Int. Cl.[4] .......................... A61K 9/50; B01J 13/02
[52] U.S. Cl. ................................ 427/213.32; 424/33; 424/35; 424/37; 427/213.3; 427/213.33; 427/213.35; 427/213.36; 514/962
[58] Field of Search ...................... 427/213.32, 213.33, 427/213.35, 213.36, 213.3; 424/35, 37, 33

[56] References Cited

U.S. PATENT DOCUMENTS

| | | | |
|---|---|---|---|
| 3,037,849 | 6/1962 | Frint et al. | 423/206 T X |
| 3,043,782 | 7/1962 | Jensen | 427/213.35 |
| 3,242,051 | 3/1966 | Hiestand et al. | 264/4.3 X |
| 3,533,958 | 10/1970 | Yurkowitz | 427/213.32 |
| 3,574,132 | 4/1971 | Mosier et al. | 264/4.3 |
| 3,725,014 | 4/1973 | Poncha et al. | 423/206 T X |
| 4,460,563 | 7/1984 | Calanchi | 427/213.32 X |

FOREIGN PATENT DOCUMENTS 0676316  7/1979  U.S.S.R. .......................... 427/213.32

OTHER PUBLICATIONS

The Merck Index, Tenth Edition, Published by Merck & Co., Inc., Rahway, N.J., 1983, pp. 202 and 569.
O. Siddiqui et al., "Physical Factors Affecting Microencapsulation by Simple Coacervation of Gelatin", *J. Pharm. Pharmacol.*, 35, 70–73 (1983).
Chih-Ming James Chen, "Production of Drugs in Small Particle Form", Dissertation, The Ohio State University, 1981.
G. I. Mukhayer et al., "Interactions between Large Organic Ions of Opposite Charge: VI. Coacervation in Mixtures of Sodium Dodecyl Sulfate and Benzyltriphenylphosphonium Chloride", *J. Coll. and Int. Sci.*, 66, 110–117 (1978).
J. R. Nixon et al., "The In Vitro Evaluation of Gelatin Coacervate Microcapsules", *J. Pharm. Pharmac.*, 23, 147S–155S (1971).
P. L. Madan, "Clofibrate Microcapsules: III. Mechanism of Release", *Drug Development and Industrial Pharmacy*, 6, 629–644 (1980).
H. P. Merckle and P. Speiser, "Preparation and In Vitro Evaluation of Cellulose Acetate Phthalate Coacervate Microcapsules", *J. Pharm. Sci.*, 62, 1444–1448 (1973).
A. S. Michaels et al., "The Effect of Surface Active Agents on Crystal Growth Rate and Crystal Habit", *J. Phys. Chem.*, 64, 13–19 (1960).
V. K. LaMer, et al., "Theory Production and Mechanism of Formation of Monodispersed Hydrosols", *J. Amer. Chem. Soc.*, 72, 4847–4854 (1950).
P. L. Madan, "Microencapsulation: I. Phase Separation or Coacervation", *Drug Development and Industrial Pharmacy*, 4, 95–116 (1978).
P. L. Madan, "Microencapsulation: II. Interfacial Reactions", *Drug Development and Industrial Pharmacy*, 4, 289–304 (1978).
McCutcheon's Detergents & Emulsifiers, 1973 No. American Edition, Publ. by McCutcheon's Division, Allured Publishing Corp., Ridgewood, NJ, 1973, p. 173.
Poorly Water–Soluble Drugs by Crystallization in Aqueous Surfactant Solutions I: Sulfathiazole, Prednisone, and Chloramphenicol", *J. Pharm. Sci.*, 65, 1702–1704 (1976).
K. Ikeda, et al., "Micellar Interaction of Tetracycline Antibiotics", *Chem. Pharm. Bull.*, 25, 1067–1072 (1977).

*Primary Examiner*—Richard D. Lovering

[57] ABSTRACT

Process for the formation and the simultaneous encapsulation of small particles of a compound from solution which comprises:
(a) dissolving said compound in a first solvent;
(b) preparing a solution of encapsulating material and an electrolyte in a second solvent which is miscible with the first solvent and in which the compound to be encapsulated is more or less insoluble, in an amount which is effective, but present in an amount just insufficient to cause coacervation of the encapsulating material without interacting with it;
(c) mixing the solutions from step (a) and (b) while stirring to cause the concurrent precipitation of the compound as small particles and formation of a coacervate of the encapsulating material; and
(d) gelling the encapsulating material.

10 Claims, No Drawings

SMALL PARTICLE FORMATION AND ENCAPSULATION

The present invention is concerned with the simultaneous formation and encapsulation of small particles from solutions of compounds whose solubility is greater in one solvent than in another. The process is preferably used to prepare a readily soluble encapsulated pharmaceutically active compound.

BACKGROUND OF THE INVENTION

From a pharmaceutical point of view, the smaller the particle size of a relatively insoluble drug the greater is its rate of solution and as a rule, the greater is its bioavailability (J. H. Fincher, J. Pharm. Sci., 57, 1825 (1968)). To this end, small particles are conventionally formed by mechanical subdivision of bulk matter or by aggregation of small molecules or ions (D. J. Shaw, "Introduction to Colloid and Surface Chemistry", 3rd Ed., Butterworths, London, 1980, Chapter 1). The production and applications of microcapsules for medical and technical use have been extensively reviewed (L. A. Luzzi, J. Pharm. Sci., 59, 1367 (1970); A. Kondo, "Microcapsule Processing and Technology", Marcel Dekker, New York (1979); J. E. Vandegaer, "Microencapsulation: Processes and Applications", Plenum Press, New York (1976); J. R. Nixon, "Microencapsulation", Marcel Dekker, New York (1976); J. A. Bakan and J. L. Anderson, in "The Theory and Practice of Industrial Pharmacy", Second Ed., (Ed. L. Lachman, et al.), Lea & Febiger, Philadelphia, 1976, p. 420; M. H. Gutcho, "Microcapsules and Microencapsulation Techniques", Noyes Data Corp., New Jersey, (1976)).

SUMMARY OF THE INVENTION

A method has now been found which involves the formation of small core particles of an active compound from solution and the concurrent encapsulation of the core particles in a coacervate of the encapsulating material when the solvent system is altered. This process of encapsulation of an active compound in a natural or synthetic polymer protects and stabilizes the active core compound.

The new method for encapsulating organic compounds whose solubility varies significantly from one solvent system to another comprises:

(a) dissolving said compound in a first aqueous or nonaqueous solvent;

(b) preparing a solution of encapsulating material and an electrolyte in a second solvent which is miscible with the first solvent and in which the compound to be encapsulated is more or less insoluble, in an amount which is effective (but present in an amount just insufficient) to cause coacervation of the encapsulating material without interacting with it;

(c) mixing the solutions from step (a) and (b) while stirring to cause the concurrent precipitation of the compound as small particles and formation of a coacervate of the encapsulating material;

(e) gelling the encapsulating material; and (f) hardening the encapsulating material. If necessary to cause precipitation additional quantities of the electrolyte used in step (b) may be added.

After the first encapsulation the microcapsules can be redispersed and a second wall can be deposited over the first.

In this process, coacervation of the encapsulating material is believed to result from the change of solvent character of the solution, which disturbs the system, when taken together with the electrolyte initially present and causes coacervation.

Suitable pharmaceutically active compounds whose solubility decreases from one solvent system to another, are, for example, budesonide, felodipine, bacampicillin, griseofulvin, indomethacin, erythromycin, theophylline, salicylic acid, nifedipine, remoxipride, chlorzoxazone, lidocaine and alaproclate.

A suitable encapsulating material which will form a coacervate is, for example, gelatin (preferably of the type B; acid processed), methylcellulose, hydroxypropyl methylcellulose, sodium carboxymethylcellulose, ethylcellulose, cellulose acetate phthalate and polyvinylpyrrolidone. A suitable electrolyte which is effective to cause coacervation of the encapsulating material without interacting with it is, for example, sodium sulfate solution, preferably a 5–30% aqueous solution which may also contain a suitable cosolvent, for example, an alcohol or a wetting agent at about 0–10%. The compound, encapsulating material, wetting agent and electrolyte can be combined in step (a) in ratios of about (0.1–6):(0.1–4):(0.1–10):(0.4–48).

The gelling of the encapsulating material can be achieved by treatment of the encapsulating material with cold (5° C.) $Na_2SO_4$ solution. If polyvinylpyrrolidone is used as the encapsulating material gelling can also be achieved by a number of other methods, for example:

1. application of heat (to 60° C.);
2. addition of hydrochloric acid, 0.05N–1.0 N (10 ml 0.1 M HCl/ml) to the mixture to be gelled;
3. application of heat (40°–45° C.) plus addition of sodium sulfate solution;
4. application of heat plus addition of hydrochloric acid;
5. application of heat (40°–45° C.) plus addition of hydrochloric acid and sodium sulfate.

If ethylcellulose is used as the encapsulating material temperature change can be used to cause coacervation of the ethylcellulose.

Once formed, the gelled or "unhardened" microcapsules can be hardened by first centrifuging a suspension of the microcapsules to produce a concentrated suspension. The concentrated microcapsules are washed twice with water by redispersing and centrifuging. The washed microcapsules are then redispersed in water, formaldehyde solution or glutaraldehyde solution is added and the suspension allowed to stand at room temperature for 15–20 hours. The suspension is centrifuged, the microcapsules washed twice with water, following which they are dehydrated by being redispersed in a water/isopropanol (or other suitable alcohol) mixture, filtered, washed twice with alcohol, filtered and dried. The encapsulated particles formed by this process are less than 100 $\mu$m, preferably less than 10 $\mu$m; and the core particles are less than 25 $\mu$m, preferably less than 1 $\mu$m.

In an alternate embodiment, a suitable acid may be used to convert the free base of a compound to its salt form or for the free acid to be converted to the salt form by the addition of a base, prior to step (b).

For some applications a double wall microcapsule is useful. In forming a double wall, the single walled microcapsule is redispersed and a second wall is deposited over the first.

DETAILED DESCRIPTION OF THE INVENTION

According to one embodiment of the invention, the process comprises the following steps which are performed at about 55° C.

(a) dissolving a pharmaceutically active compound in a first solvent;

(b) adding to the solution obtained in step a, a solution of gelatin and sodium sulfate in a second solvent which is miscible with the first solvent and in which the active compound is more or less insoluble while keeping the solution under constant agitation which results in a suspension of encapsulated pharmaceutically active small particles and coacervation of the gelatin; and (c) adding a solution of sodium sulfate.

The suspension is then poured into cold sodium sulfate solution and stirred at the temperature of an ice bath. This procedure causes "gelling" of the liquid gelatin shell of the microcapsules. The microcapsules are then collected, for instance, by centrifugation; or (d) the suspension is centrifuged and washed twice with water, centrifuged, dispersed into water, formaldehyde or glutaraldehyde solution is added under stirring which is continued for several hours, or the suspension can be allowed to stand at room temperature. This procedure causes hardening of the gelled microcapsule shell. The suspension is centrifuged, the microcapsules washed twice with water, redispersed in water with stirring, isopropanol added, filtered, washed twice with isopropanol, filtered and dried. This procedure causes dehydration of the hardened microcapsules. The formaldehyde should be added as a 5–37% solution, preferably a 37% (w/w) solution. The alcohol can be any water-miscible alcohol, preferably isopropanol, and the mixture with water can be 5–50% (w/w) isopropanol.

The process of forming microcapsules according to this invention can be illustrated by the following examples.

EXAMPLE 1

A solution consisting of 0.38 g felodipine and 2.0 ml of polyethylene glycol 400 was kept under constant agitation with a magnetic stirrer while a solution consisting of 1.25 g gelatin (type B:acid processed), 4 g of sodium sulfate and 50 ml of water was added. This procedure resulted in a white suspension of microencapsulated felodipine particles. An additional 50 ml of 20% sodium sulfate solution was added and the suspension was then stirred for an additional 15 minutes, following which it was poured into 200 ml of cold (5° C.) 7% sodium sulfate solution, and stirred for 30 minutes at ice-bath temperature. This procedure caused gelling of the liquid gelatin shell of the microcapsules. The suspension of gelled microcapsules was centrifuged and washed twice with water by redispersing and centrifuging. The microcapsules were redispersed in 50 ml of water, 5 ml of 37% formaldehyde solution added under stirring and the suspension allowed to stand at room temperature for 15–20 hours. This procedure caused hardening of the "gelled" gelatin shell of the microcapsules. The suspension was centrifuged and the microcapsules were washed again twice with water, following which they were redispersed in 10 ml of water with stirring and 50 ml of isopropanol added slowly. The suspension was filtered and washed twice with 50 ml of isopropanol, filtered and dried in an oven at 35° C. This procedure caused dehydration of the hardened capsules. The dry microcapsules were stored in well-closed containers at room temperature. The entire process was monitored by observation of samples in the optical microscope. The microcapsules were of asymmetric appearance and of a size less than 10 μm.

A schematic diagram of the entire process according to Example 1 is illustrated below:

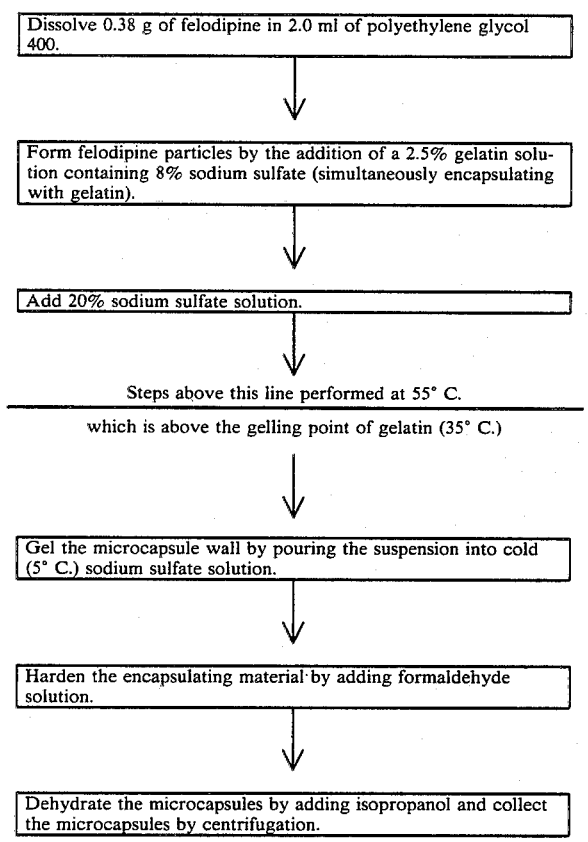

EXAMPLE 2

A solution consisting of 0.7 g of budesonide in 2 ml of N,N-dimethylformamide was freshly prepared. While this solution was held under constant agitation (500 rpm) with a magnetic stirrer, a second solution consisting of 50 ml of 2% methylcellulose and 6 ml of 20% sodium sulfate was added. The stirring speed was changed to 1270 rpm immediately after mixing the two solutions and stirring was continued at room temperature for 15 minutes. The microencapsulated budesonide particles were collected by centrifugation, washed twice with 25 ml of water, and freeze-dried. Both methylcellulose 25 cps (Dow Chemical Co.) and METHOCEL A 15LV Premium (Dow) were studied.

The entire procedure was monitored by observation of samples in the optical microscope. A schematic diagram of the process is illustrated below:

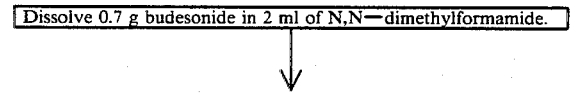

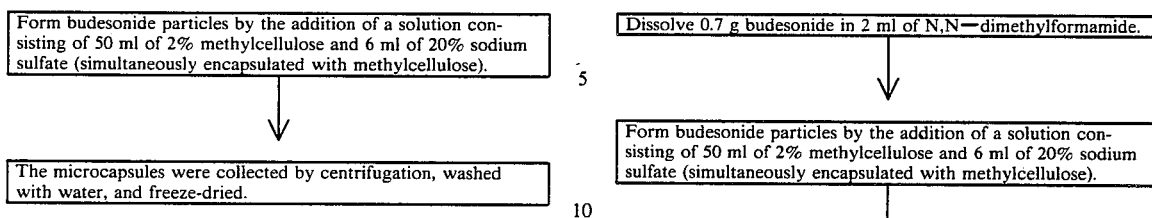

EXAMPLE 3

The procedure for the preparation of hydroxypropyl methylcellulose microcapsules was similar to that for the methylcellulose microcapsules described in Example 2. A solution considting of 0.35 g of budesonide in 1 ml of N,N-dimethylformamide was freshly prepared. While this solution was held under constant agitation (500 rpm) with a magnetic stirrer, a second solution consisting of 100 ml of 0.5% hydroxypropyl methylcellulose (METHOCEL F4M Premium, Dow) and 22 ml of 20% sodium sulfate was added. The stirring speed was changed to 1270 rpm immediately after mixing the two solutions and stirring was continued at room temperature for 20 minutes. The microencapsulated budesonide particles were collected by centrifugation, washed twice with water (50 ml and 20 ml in sequence), and freeze-dried.

The entire procedure was monitored by observation of samples in the optical microscope. A schematic diagram of the process is illustrated below:

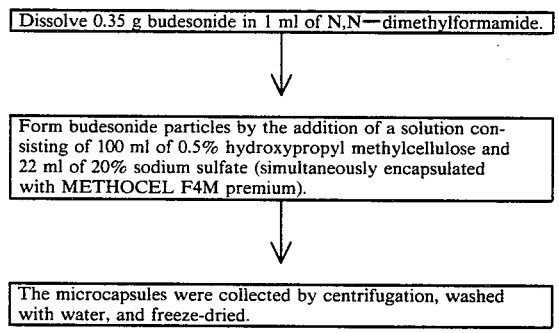

EXAMPLE 4

Single-wall methylcellulose microcapsules were prepared first by the process described in Example 2 using methylcellulose 25 cps (Ruger Chemical Co.). After the single wall microcapsules were collected by centrifugation and washed once with 25 ml of water, they were redispersed in 10 ml of water and mixed with 40 ml of 0.625% hydroxypropyl methylcellulose solution (METHOCEL F4M Premium, Dow). While under constant agitation (800 rpm) with a magnetic stirrer, 13.5 ml of 20% sodium sulfate solution was added dropwise. The stirring was continued at 800 rpm for 3 minutes and at 200 rpm for an additional 20 minutes. The microcapsules were collected by centrifugation, washed twice with water, and freeze-dried.

The entire procedure was monitored by observation of samples in the optical microscope. A schematic diagram of the process is illustrated below:

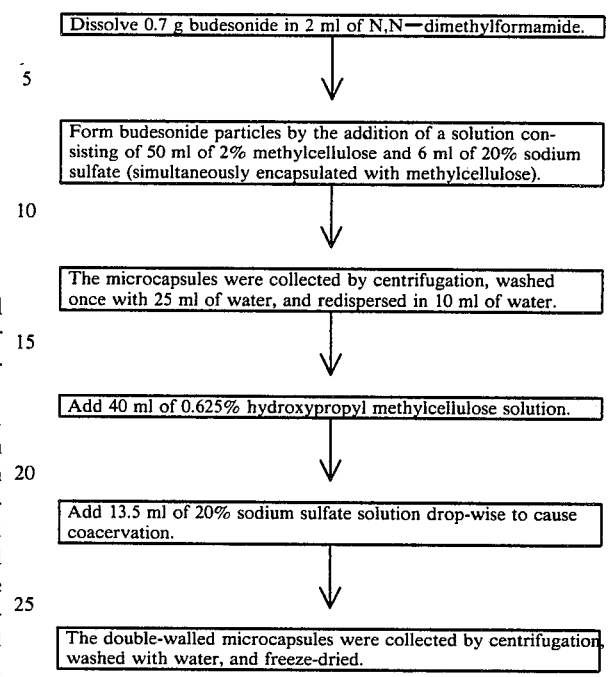

EXAMPLE 5

A solution of ethylcellulose in cyclohexane was prepared by heating and stirring the desired amount of ethylcellulose (ETHOCEL 100 cps, Dow) and surfactant in 20 ml of cyclohexane. When the ethylcellulose and surfactant were dissolved and the temperature was above 75° C., this hot solution was poured immediately into a suspension of microcapsules freshly prepared by sonicating 0.2 g of dry single-wall microcapsules in 5 ml of cyclohexane for one minute. The singlewall microcapsules used in this Example were coated with methylcellulose 25 cps (Ruger Chemical Co.) according to the process described in Example 2.

The mixture was first stirred at room temperature at a speed of 400 rpm. After cooling down to 25°-28° C. (approximately 30 minutes), it was placed in a 10° C. water bath, stirred for 5 more minutes, and then mixed with 25 ml of hexane. This mixture was continuously stirred at 400 rpm for another 5 minutes. The resultant double wall microcapsules were washed twice with 25 ml of hexane by decanting the supernate, and collected by filtration. The microcapsules were dried in air overnight and then in a reduced-pressure oven at 40° C. for 30 minutes. A schematic diagram of the process is illustrated below:

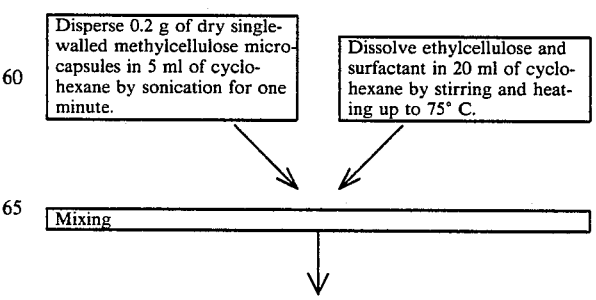

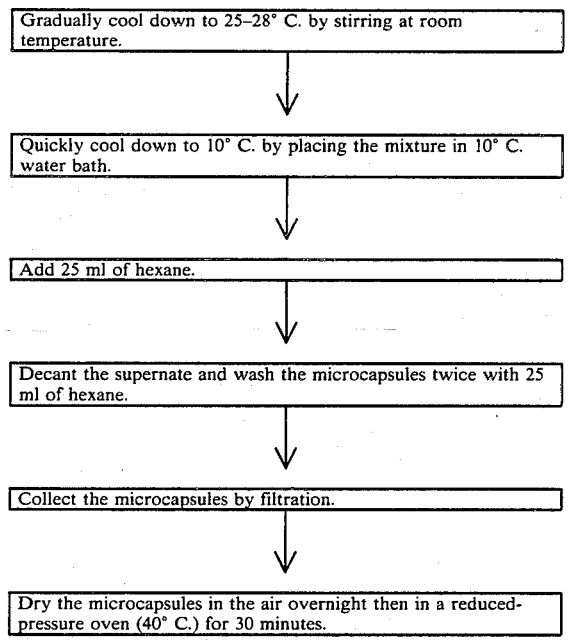

We claim:

1. A process for encapsulating an organic compound whose solubility is greater in a first solvent than in a second solvent which process comprises:
   (a) dissolving said compound in a first solvent;
   (b) preparing a solution of encapsulating material and an electrolyte in a second solvent which is miscible with the first solvent and in which the compound to be encapsulated is more or less insoluble, in an amount which is effective, but which electrolyte is present in an amount just insufficient to cause coacervation of the encapsulating material without interacting with it;
   (c) mixing the solutions from step (a) and (b) while stirring to cause the concurrent precipitation of the compound as small particles and formation of a coacervate of the encapsulating material; and
   (d) gelling the encapsulating material.

2. A process according to claim 1 wherein the encapsulated material is hardened.

3. A process according to claim 1 wherein the encapsulated material is redispersed in a liquid and encapsulated in a different encapsulating material.

4. A process according to claim 1 wherein additional electrolyte is added after step (b) to cause concurrent precipitation of the compound as small particles and formation of a coacervate of the encapsulating material.

5. A process according to claim 1 wherein the compound is pharmaceutically active.

6. A process according to claim 5, wherein the pharmaceutically active compound is selected from the group consisting of budesonide and felodipine.

7. A process according to claim 1 wherein a wetting agent is used in step a.

8. A process according to claim 1 wherein, if needed, the temperature is controlled in step c.

9. A process according to claim 8, wherein the ratio of encapsulating material to wetting agent to electrolyte is about (0.1–6):(0.1–4):(0.1–10):(0.4–48).

10. A process according to claim 1, wherein the encapsulating material is selected from the group consisting of gelatin, methylcellulose, hydroxypropyl methylcellulose, sodium carboxymethylcellulose, cellulose acetate phthalate, ethylcellulose, and polyvinylpyrrolidone.

* * * * *